United States Patent [19]
Park

[11] Patent Number: 6,142,951
[45] Date of Patent: Nov. 7, 2000

[54] DIRECTIONAL BATON WITH A BREATH ANALYZER

[76] Inventor: Jun I. Park, CPO Box 5403, Seoul 100-654, Rep. of Korea

[21] Appl. No.: 09/299,120

[22] Filed: Apr. 24, 1999

[51] Int. Cl.[7] .................................................. A61B 5/08
[52] U.S. Cl. .................... 600/532; 600/543; 463/47.2; 463/47.4; 463/48
[58] Field of Search ................................ 600/532, 543; 463/47.2, 47.4, 48

[56] References Cited

U.S. PATENT DOCUMENTS

D. 404,509  1/1999  Deen ........................................ D26/37
5,424,797  6/1995  Takagi ..................................... 354/413
5,738,434  4/1998  Sun ......................................... 362/199

*Primary Examiner*—Cary O'Connor
*Assistant Examiner*—Ryan Carter
*Attorney, Agent, or Firm*—John K. Park; Park & Sutton LLP

[57] ABSTRACT

The directional baton with a breath analyzer according to this invention is divided into three sections. Three sections are head, neck, and handle, such that the head is attached to the neck and the neck is attached to the handle. The head is made from a partially transparent material, and the head houses a means for lighting the head and a means for displaying the varying levels of the alcohol content in the person's breath. The neck houses an alcohol sensor, and the handle houses the power source.

20 Claims, 3 Drawing Sheets

DIRECTIONAL BATON WITH A BREATH ANALYZER

BACKGROUND

This present invention relates to a directional baton with a breath analyzer. This invention is used to detect and test the alcohol level of a person. This invention is ideal for the law enforcement in its effort in screening the drunken drivers, but this invention should not be limited to the law enforcement use.

The directional batons are widely used, especially to direct the traffic. Also, the directional batons are used to regulate the flow of the traffic, while the law enforcement officers are screening the drivers for their blood alcohol level.

As the law enforcement officers are screening the drivers for their blood alcohol level, the officers often use breath analyzers. However, because the officers often have many instruments in their hands during the inspection, having the separate alcohol breath analyzer and the directional baton is cumbersome. Moreover, because the inspections for drunk drivers are often conducted during the evening or night hours, a need for the breath analyzer that can easily be used in dark is great.

For the foregoing reasons, there is a need for a new directional baton with a breath analyzer.

SUMMARY

This present invention relates to a directional baton with a breath analyzer. This innovative invention eliminates the need to carry both the directional baton and a breath analyzer.

The directional baton with a breath analyzer according to this invention is divided into three sections. Three sections are head, neck, and handle, such that the head is attached to the neck and the neck is attached to the handle.

The head has a top portion and a lower portion. The head is made from a partially transparent material; generally in colors of substantially orange, yellow, red, blue or green.

Housed in the head is a means for lighting the head. This can be a simple light bulb, or a light-emitting diode. This lighting means would be used to direct the traffic, especially in the dark. Moreover, at the top portion of the head can contain a flashlight.

The neck is attached to the lower portion of the head. In the neck, an alcohol sensor is attached. Although it is preferred to have the alcohol sensor attached within the neck, it is possible to mount the alcohol sensor at different locations, such as the head or the handle. The alcohol sensor should be capable of detecting the presence of the alcohol in a person's breath, and the alcohol sensor should also be capable of sending varying electrical signals indicating the level of the alcohol content in the person's breath.

The directional baton with a breath analyzer uses a means for differentiating (or the differentiating means) the variation in the electrical signal from the alcohol sensor. The differentiating means converts the electrical signals from the alcohol sensor into an indicating signal, so that the alcohol level can be illustrated by the present invention. This differentiating means can be a circuit controller that controls the displaying means (described below). It is preferred to have differentiating means attached within the neck, but it is possible to mount the differentiating means at different locations, such as the head or the handle.

The directional baton with a breath analyzer also uses a means for displaying (or the displaying means) the variation of the indicating signal to illustrate the level of the alcohol content in the person's breath. The displaying means can be a plurality of light-emitting diodes attached within the head. The inventor found that a series of five light-emitting diodes to be the best for the present invention with the head of about three inches or more in length, and that a series of two or three light-emitting diodes to be the best for the present invention with the head of about one or two inches in length.

The directional baton with a breath analyzer also has a means for lighting (lighting means) the head. This lighting means can be a separate light source, but the inventor found the use of one or more of the light-emitting diodes of the displaying means to be very effective, and this is preferred.

A variation to the present invention can be made by the use of cover to protect the alcohol sensor. This cover should be rotatably and suspendedly attached to the neck, so the alcohol sensor can be covered as the convenient to the user.

One of the benefits of this invention is that the user of the invention can use the directional baton with a breath analyzer to direct the traffic, flag a vehicle to stop, ask the driver to blow on to the alcohol sensor, and quickly obtain the blood-alcohol level very conveniently. The user would not have to switch between his or her baton and the breath tester. Moreover, because the baton and the breath analyzer are combined into one slim and convenient device, it frees the hand of the user (officer) even the baton and the breath analyzer unit is held in one hand. The user can use the free hand to write a report or even give a citation. Furthermore, the present invention can be easily slipped into the conventional baton holder (or a flashlight holder) of the user to free both hands the user without abandoning the unit.

DESCRIPTIONS OF FIGURES

These and other features, aspects, and advantages of the present invention will become better understood with regard to the following description, appended claims, and accompanying drawings where:

DETAILED DESCRIPTION

Figure 1:
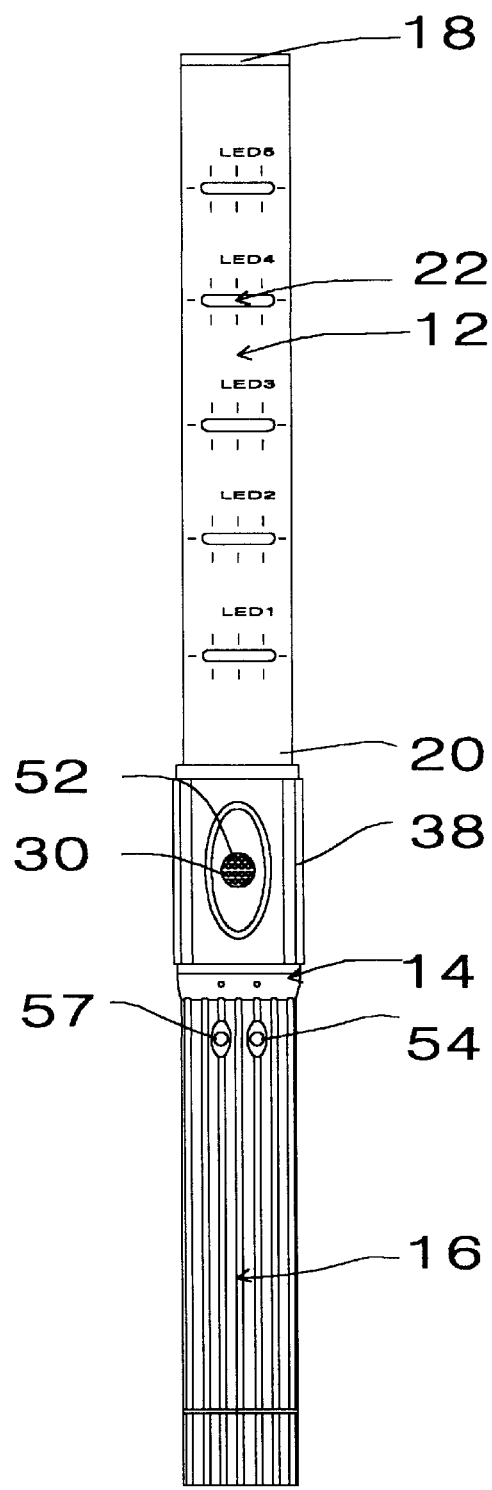
FIG. 1 is a front elevational view of the present invention.

This present invention relates to a directional baton with a breath analyzer 10. This innovative invention eliminates the need to carry both the directional baton and a breath analyzer.

Referring to the figures, this invention is divided into three sections. Three sections are a head 12, a neck 14, and a handle 16. The head 12 is attached to the neck 14, and the neck 14 is attached to the handle 16.

The head 12 has a top portion 18 and a lower portion 20. The head 12 is made from a partially transparent material; generally in colors of substantially orange, yellow, red, blue or green. An ideal material for the head 12 is partially transparent tubular plastic.

Figures 2, 2A, 2B:
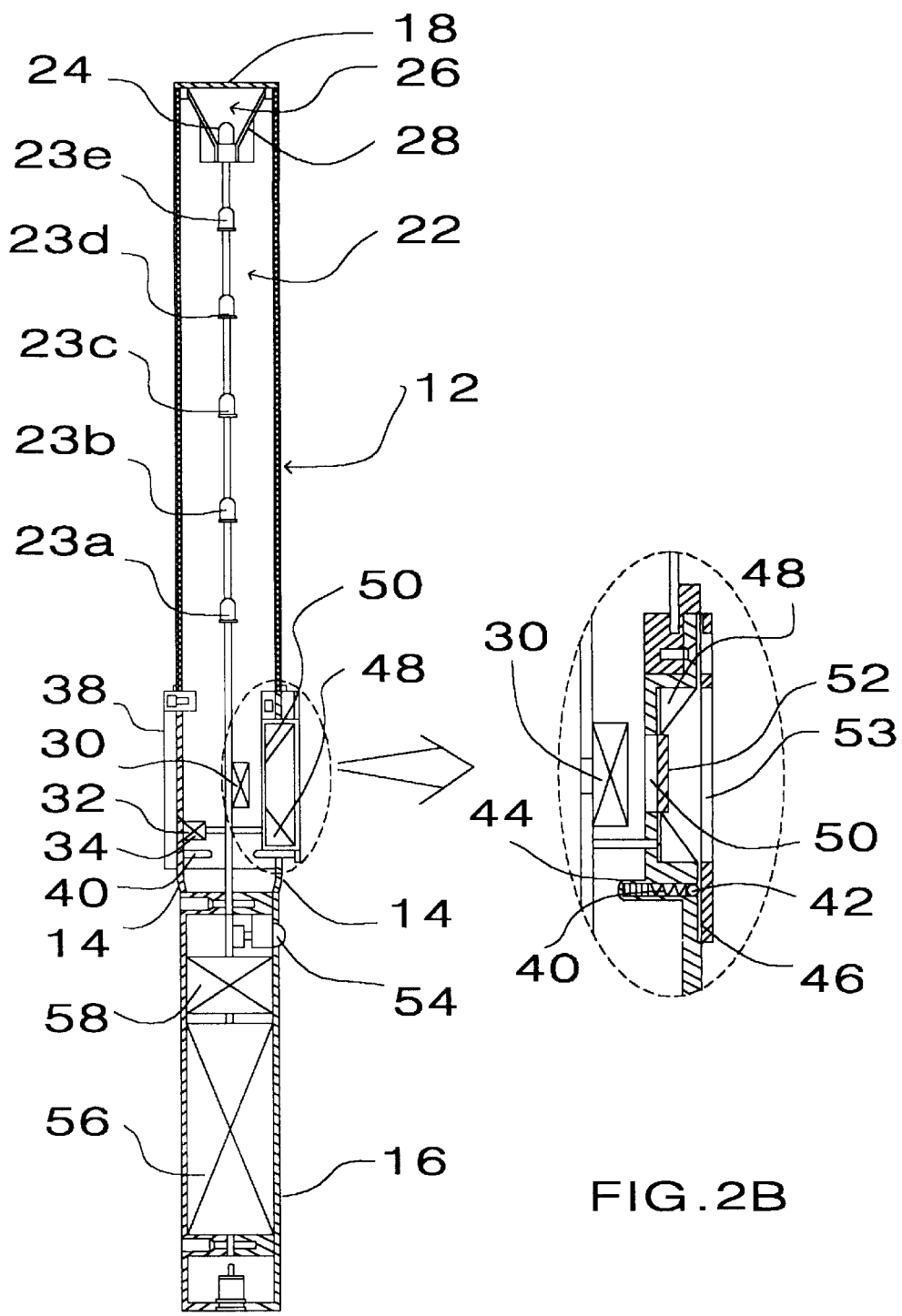
FIG. 2 is a cross-sectional view of the right side elevation of the present invention.

Enclosed within the head 12 is a means for lighting the head 12 (the lighting means 22). This can be a simple light bulb 24, or a light-emitting diode 23a, 23b, 23c, 23d, 23e. In FIG. 2, the simple light bulb 24 functions also as a flashlight 26. When the flashlight 26 functions also as the lighting means 22, then the support 28 should be such that the support 28 would allow some light to be passed through the head 12, illuminating the head 12. However, a preferred means for the lighting the head 12 is to the use of one or more light-emitting diodes 23a, 23b, 23c, 23d, 23e to illuminate the head 12.

One variation can be that the plurality of light-emitting diodes 23a, 23b, 23c, 23d, 23e is lit sequentially to have the cascading light effect. Each adjacent light can be turned on with a delay of between about 0.1 second and 0.5 second. Such sequential display of cascading lights can be very useful in directing traffic, especially in the dark, as it could be seen from a further distance. Moreover, an another option, one or more of the light-emitting diodes 23a, 23b, 23c, 23d, 23e and the flashlight 26 can be illuminated simultaneously for situations that require additional brightness.

As shown in FIG. 2, the top portion 18 of the head 12 can contain a flashlight 26. To have the most efficient use of the light from the flashlight 26, it is preferred to have the support 28 form a reflector. Therefore, this configuration of the present invention would serve as three devices (a directional baton, an alcohol sensor 30, and a flashlight 26) in one.

FIG. 1 and FIG. 2 illustrate that the neck 14 is attached to the lower portion 20 of the head 12. This neck 14 portion of the present invention houses the alcohol sensor 30. However, although it is preferred to have the alcohol sensor 30 attached within the neck 14, it is possible to mount the alcohol sensor 30 at different locations, such as within the head 12 or within the handle 16.

The alcohol sensor 30 should be capable of detecting the presence of the alcohol in a person's breath. Moreover, the alcohol sensor 30 should also be capable of sending varying electrical signals indicating the level of the alcohol content in the person's breath. Because the alcohol sensor 30 is used to measure the alcohol level in the breath, this invention can be used to prevent any transmitted diseases often associated with different methods in breath analysis.

The present invention uses a means for differentiating (or the differentiating means 32) the variation in the electrical signal from the alcohol sensor 30. The differentiating means 32 converts the electrical signals from the alcohol sensor 30 into an indicating signal, so that the alcohol level can be illustrated by the present invention. This differentiating means 32 can be a circuit controller 34 that controls the displaying means 22 (described below). It is preferred to have differentiating means 32 attached within the neck 14, but it is possible to mount the differentiating means 32 at different locations, such as the head 12 or the handle 16.

The present invention also uses a means for displaying (or the displaying means 23) the variation of the indicating signal to illustrate the level of the alcohol content in the person's breath. The displaying means can be a plurality of light-emitting diodes 23a, 23b, 23c, 23d, 23e attached within the head 12. The inventor found that a series of five light-emitting diodes 23a, 23b, 23c, 23d, 23e to be the best for the present invention with the head 12 of about three inches or more in length, and that a series of two or three light-emitting diodes 23a, 23b, 23c, 23d, 23e to be the best for the present invention with the head 12 of about one or two inches in length.

An improvement to this invention can be made such that each of the plurality of light-emitting diodes 23a, 23b, 23c, 23d, 23e indicates a range of predetermined alcohol level by being illuminated. As an example, the first light-emitting diode 23a would light up for detecting no alcohol content, the second light-emitting diode 23b would light up for having more than 0.0% but less than about 0.025% blood alcohol level, the third light-emitting diode 23c would light up for having more than 0.025% but less than about 0.050% blood alcohol level, the fourth light-emitting diode 23d would light up for having more than 0.050% but less than about 0.1% blood alcohol level, and the fifth light-emitting diode 23e would light up for having more than 0.1% blood alcohol level.

Another example would be the use of combination of two or more light-emitting diodes 23a, 23b, 23c, 23d, 23e to indicate the blood alcohol level higher than 0.1%; such as the fifth light-emitting diode 23e and the first light-emitting diode 23a would both light up for more than 0.1% but less than about 0.125% blood alcohol level. Similarly, the fifth light-emitting diode 23e and the third light-emitting diode 23c can both light up for more than 0.15% but less than about 0.2% blood alcohol level.

The lighting of the light-emitting diodes 23a, 23b, 23c, 23d, 23e should be predetermined according to the earlier assigned alcohol level relative to the local law. The circuit controller 34 can be programmed to adjust the assigned alcohol level according to the local law, or according to the discretion of the user.

Another improvement to the present invention can be made by use of an alarm 36 that produces a predetermined sound when an assigned alcohol level is detected. Moreover, the alarm 36 can also be controlled by the circuit controller 34, so that the alarm 36 would produce different predetermined sounds when the assigned alcohol level for each predetermined sound is detected.

A variation to the present invention can be made by the use of cover 38 to protect the alcohol sensor 30. This cover 38 should be rotatably and suspendedly attached to the neck 14, so the alcohol sensor 30 can be covered according to the convenience of the user. FIG. 2 shows a means for suspending (suspending means 40) the cover 38 over the neck 14 while allowing the cover 38 to be rotatably attached to the neck 14. The suspending means 40 generally comprises of a ball 42 supported by a spring 44 so that the ball 42 pushes onto the inner surface 46 of the cover 38. The use of the ball 42 and the spring 44 allows the cover 38 to be rotatably and suspendedly attached to the neck 14.

As another improvement, the present invention can have the neck 14 further comprising a luminous area 48 having a hole 50, and a grill 52 over the hole 50, wherein the grill 52 is directly over the alcohol sensor 30 so that the grill 52 protects the alcohol sensor 30 during the use of the alcohol sensor 30. The luminous area 48 can be illuminated in the dark so the grill 52 over the alcohol sensor 30 can be highlighted. The illumination of the luminous area 48 is helpful in the dark areas.

Figure 3:
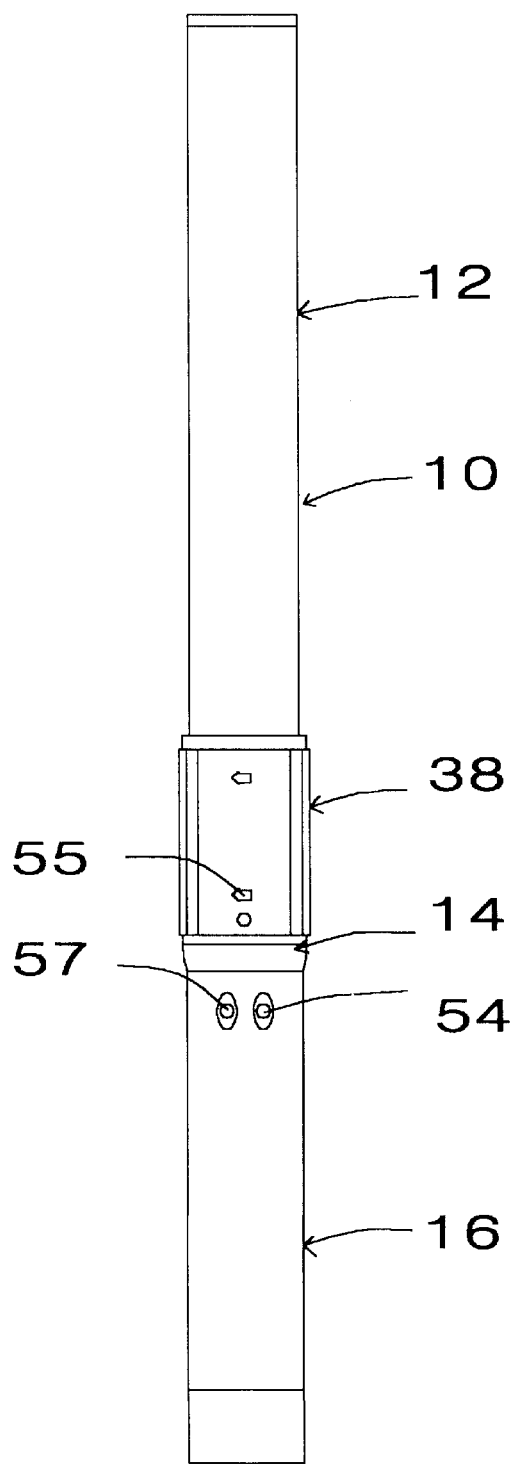
FIG. 3 is a front elevational view of the present invention showing the cover covering the alcohol sensor.

FIG. 1 and FIG. 2 illustrate the cover 38 having an opening 53. When the opening 53 is directly over the hole 50 and the grill 52, then the alcohol sensor 30 is exposed through the grill 52, and the alcohol sensor 30 can then be used to detect the alcohol content of the breath. However, as shown in FIG. 3, the cover 38 can be rotated so that the hole 50 and the grill 52 is covered by the cover 38, concealing the alcohol sensor 30 for protection. Arrows 55 are used to indicate that the cover 38 is rotatably attached to the neck 14. The rotating direction of the cover 38 is shown by the arrows 55, but the direction of the rotation can be both to the right or to the left.

The present invention can further comprise of a sensor switch 54 connected to the alcohol sensor 30. The sensor switch 54 would regulate the flow of the electricity to the alcohol sensor 30, the circuit controller 34, and the plurality of light-emitting diodes 23a, 23b, 23c, 23d, 23e. Moreover, the present invention can also comprise of a flashlight switch 57 connected to the flashlight 26. The flashlight switch 57 would regulate the flow of the electricity to the to the flashlight 26. Both the sensor switch 54 and the flashlight switch 57 are ideally located on the handle 16.

In addition to the sensor switch 54 and the flashlight switch 57, the handle 16 can be used to house a power source. The power source can be a single or a combination of conventional single-use batteries or rechargeable battery. The use of the rechargeable battery as the rechargeable power source 56 is preferred. A power regulator 58 is highly recommended, especially when the rechargeable power source 56 is used, because the alcohol sensor 30 can be sensitive to the fluctuation of the electrical voltage or the current.

One of the benefits of this invention is that the user of the invention can use the present invention to direct the traffic, flag a vehicle to stop, ask the driver to blow on to the alcohol sensor 30, and quickly obtain the blood-alcohol level very conveniently. The user would not have to switch between his or her baton and the breath tester. Moreover, because the baton and the breath analyzer are combined into one slim and convenient device, it frees the hand of the user even the baton and the breath analyzer unit is held in one hand. The user can use the free hand to write a report or even give a citation. Furthermore, the present invention can be easily slipped into the conventional baton holder of the user to free both hands the user without abandoning the unit.

Although the invention has been described in considerable detail with reference to certain preferred versions thereof, other versions are possible. For example, the head 12 can comprise of a plurality of telescoping pieces for easier storage. Such a variation would require flexible connection among the light-emitting diodes 23a, 23b, 23c, 23d, 23e.

What I claim is:

1. A directional baton with a breath analyzer comprising:
    a) a handle;
    b) a neck attached to the handle;
    c) a head having a top portion and a lower portion, wherein the lower portion is attached to the neck;
    d) an alcohol sensor attached within the neck, the head or the handle, wherein the alcohol sensor is capable of detecting the presence of the alcohol in a person's breath, and wherein the alcohol sensor is also capable of sending varying electrical signals indicating the level of the alcohol content in the person's breath;
    e) a means for differentiating the variation in the electrical signal from the alcohol sensor, wherein the differentiating means converts the electrical signals from the alcohol sensor into an indicating signal, and wherein the differentiating means is attached within the handle, the neck or the head;
    f) a means for displaying the variation of the indicating signal to represent the level of the alcohol content in the person's breath, and wherein the displaying means is attached within the head; and
    g) a means for lighting the head attached to the head.

2. A directional baton with a breath analyzer of claim 1 wherein the head is formed by a partially transparent material, and wherein the alcohol sensor is attached within the neck, and wherein the differentiating means is also attached within the neck.

3. A directional baton with a breath analyzer of claim 2 wherein the head is formed by a partially transparent material that is substantially orange, yellow, red, blue, or green in color.

4. A directional baton with a breath analyzer of claim 3 wherein the displaying means is a plurality of light-emitting diodes attached within the head.

5. A directional baton with a breath analyzer of claim 4 wherein each of the plurality of light-emitting diodes indicates a range of predetermined alcohol level by being illuminated.

6. A directional baton with a breath analyzer of claim 5 further comprises of an alarm that produces a predetermined sound when an assigned alcohol level is detected.

7. A directional baton with a breath analyzer of claim 6 wherein the alarm can produce different predetermined sound when the assigned alcohol level for each predetermined sound is detected.

8. A directional baton with a breath analyzer of claim 7 wherein the differentiating means is a circuit controller that controls one or more of the plurality of light-emitting diodes.

9. A directional baton with a breath analyzer of claim 8 wherein the circuit controller can also adjust the assigned alcohol level according to the local law.

10. A directional baton with a breath analyzer of claim 9 wherein the lighting means is one or more of the plurality of light-emitting diodes of the indicating means.

11. A directional baton with a breath analyzer of claim 10 wherein the lighting means is illuminating each of the plurality of light-emitting diodes sequentially.

12. A directional baton with a breath analyzer of claim 11 further comprises a flashlight attached to the top portion.

13. A directional baton with a breath analyzer of claim 12 further comprises of a cover over the alcohol sensor, wherein the cover is rotatably attached to the neck, so the cover protects the alcohol sensor when the alcohol sensor is not in use.

14. A directional baton with a breath analyzer of claim 13 further comprises of a sensor switch connected to the alcohol sensor, so that the sensor switch would regulate the flow of the electricity to the alcohol sensor, the circuit controller, and the plurality of light-emitting diodes.

15. A directional baton with a breath analyzer of claim 14 further comprises of a flashlight switch connected to the flashlight, so that the flashlight switch would regulate the flow of the electricity to the flashlight.

16. A directional baton with a breath analyzer of claim 15 further comprises of a rechargeable power source housed within the handle.

17. A directional baton with a breath analyzer of claim 16 further comprises of a power regulator connected to the rechargeable power source.

18. A directional baton with a breath analyzer of claim 17 wherein the neck further comprises of a luminous area having a hole, and a grill over the hole, wherein the grill is directly over the alcohol sensor so that the grill protects the alcohol sensor during the use of the alcohol sensor, and wherein the luminous area can be illuminated in the dark so the grill over the alcohol sensor can be highlighted.

19. A directional baton with a breath analyzer of claim 18 further comprises of a means for suspending the cover over the neck while allowing the cover to be rotatably attached to the neck.

20. A directional baton with a breath analyzer of claim 19 wherein one or more of the light-emitting diodes and the flashlight can be illuminated simultaneously.

* * * * *